United States Patent [19]

Seamons et al.

[11] Patent Number: 5,053,208
[45] Date of Patent: Oct. 1, 1991

[54] CONTACT LENS DISINFECTING CONTAINER STRUCTURE

[75] Inventors: Kenneth R. Seamons, Marietta; Stephen D. Prestwood, Roswell; Herbert L. Balcome, Sawanee, all of Ga.

[73] Assignee: Ciba-Geigy Corporation, Ardsley, N.Y.

[21] Appl. No.: 305,102

[22] Filed: Jan. 31, 1989

[51] Int. Cl.$^5$ .............................. A61L 2/18
[52] U.S. Cl. .................... 422/300; 206/222; 422/292
[58] Field of Search ........... 422/294, 102, 99, 30, 422/28, 300, 292, 61; 206/222; 215/DIG. 8

[56] References Cited

U.S. PATENT DOCUMENTS

| | | | |
|---|---|---|---|
| 2,275,567 | 3/1942 | Smith | 215/DIG. 8 X |
| 2,653,609 | 9/1953 | Smith | 206/222 X |
| 3,475,102 | 10/1969 | Larsen | 422/102 X |
| 4,103,772 | 8/1978 | Wiegner | 206/222 |
| 4,264,007 | 4/1981 | Hunt | 206/222 X |
| 4,341,948 | 7/1982 | Sundström et al. | 422/307 X |
| 4,637,919 | 1/1987 | Ryder et al. | 422/300 |
| 4,654,127 | 3/1987 | Baker et al. | 422/102 X |
| 4,757,916 | 7/1988 | Goncalves | 215/DIG. 8 |
| 4,785,931 | 11/1988 | Weir et al. | 206/222 |
| 4,927,605 | 5/1990 | Dorn et al. | 422/102 |

Primary Examiner—Robert J. Warden
Assistant Examiner—Amaha L. Santiago
Attorney, Agent, or Firm—Wenderoth, Lind & Ponack

[57] ABSTRACT

A contact lens disinfecting kit having an open topped lens container, an elongated piercer mounted in the lens container in an upright position and having piercing portions thereon projecting to the vicinity of the open top of the lens container, the piercer dividing the interior of the lens container into two separate contact lens receiving parts, and an open topped solution container attached to the lens container for being foldable over against the lens container with the open top thereof facing the open top of the lens container and having a shape with a peripheral edge around the open top thereof which fits snugly into the open top of the lens container. A sterilizing or disinfecting solution is contained in the solution container, and a pierceable cover is sealed to the edge of the solution container around the open top thereof, the piercer projecting sufficiently toward the solution container when the solution container is folded over against the lens container to pierce the pierceable cover. A catalyst is provided in the lens container for decomposing the sterilizing agent in the solution.

10 Claims, 3 Drawing Sheets

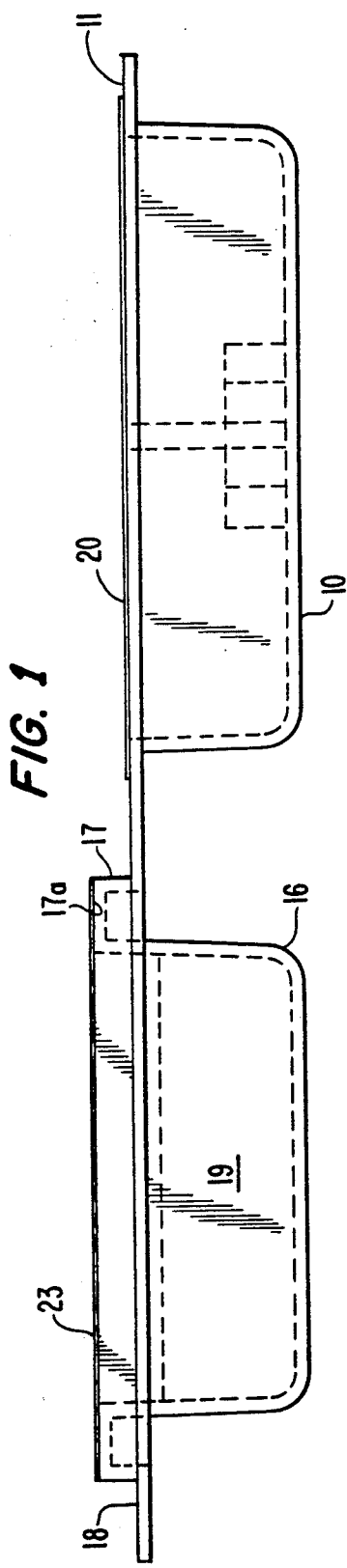
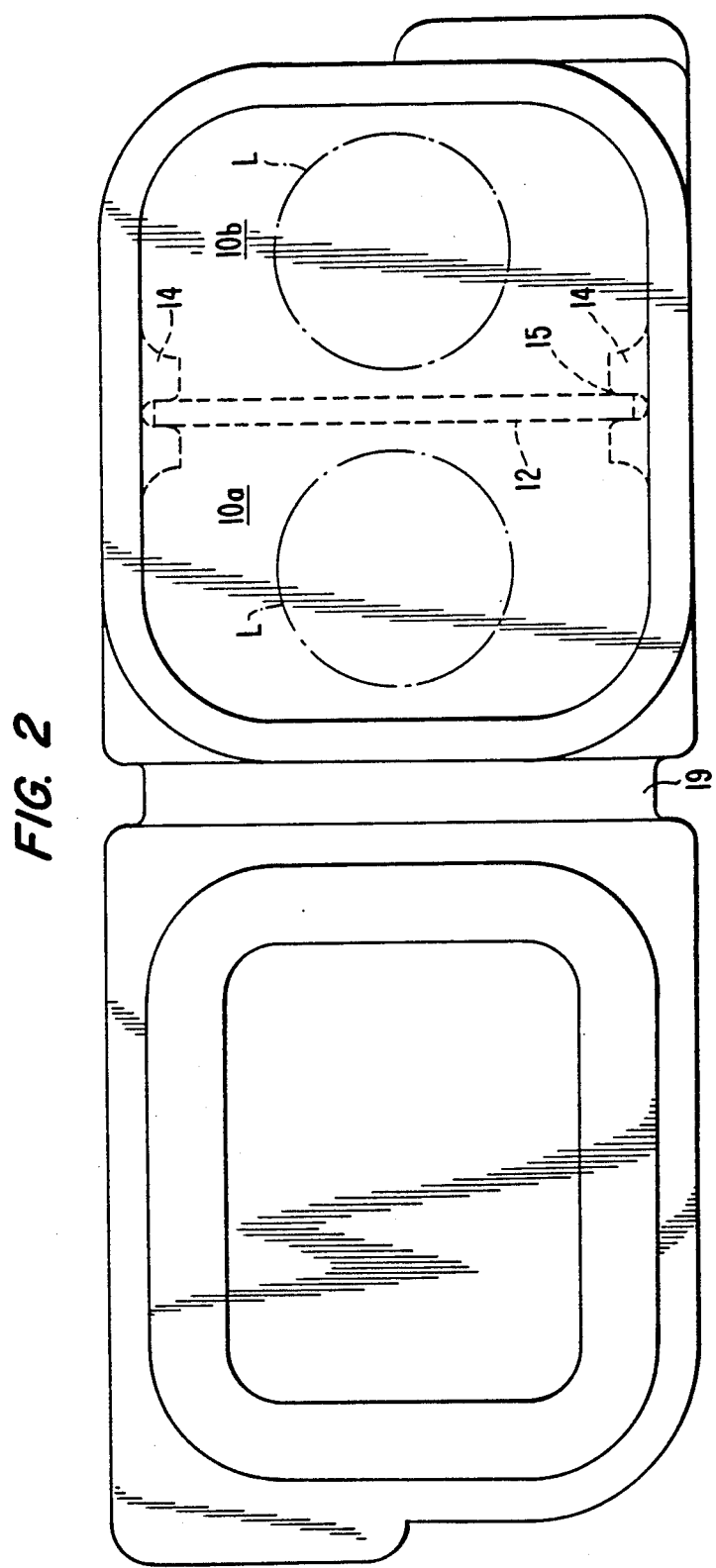

CONTACT LENS DISINFECTING CONTAINER STRUCTURE

This invention relates to a contact lens disinfecting container structure, and more particularly to such a container structure which is a one-time-use type structure which is to be discarded after one use.

BACKGROUND OF THE INVENTION

Since the advent of contact lenses, it has been the practice to store the lenses in container-like lens storage devices, and to provide for the use of a disinfecting or sterilizing solution, and/or a rinsing solution which can be poured into and out of the storage device for cleaning the lenses, disinfecting the lenses, and then rinsing the disinfecting solution from the lenses, or neutralizing the disinfecting solution remaining on the lenses.

Recently, a sterilizing or disinfecting treatment for contact lenses has been proposed, which utilizes an aqueous hydrogen peroxide solution as a sterilizing or disinfecting solution, and following the immersion of the lenses in such a solution, and the removal from such solution, the lenses are immersed in a neutralizing solution to turn the residual disinfecting solution into a saline solution. This is accomplished by, for example, using a neutralizer which decomposes the residual hydrogen peroxide into oxygen and water, the neutralizer containing a salt, which makes the resulting water saline. Examples of such a system are shown in U.S. Pat. Nos. 4,521,375 and 4,568,517. Another recently developed system of the same type provides, as the sterilizing solution, a saline hydrogen peroxide solution, and the container-like device is provided with a catalyst, for example platinum, so that when the hydrogen peroxide and salt solution is poured into the device, the platinum, acting as a catalyst, decomposes the hydrogen peroxide into water and oxygen, leaving the saline solution as the storage solution.

These systems have, to date, been used with containers which, after they have been used, are cleaned out, by rinsing with water, for example, and then reused over and over again.

It is desirable, however, to provide for a one-time-use container structure which can be used once and then discarded. This is very useful, for example, for persons who are traveling, or persons who need to sterilize or disinfect their contact lenses when they are away from the place where the reusable container device is kept.

OBJECTS AND BRIEF SUMMARY OF THE INVENTION

It is an object of the present invention to provide a contact lens disinfecting container structure which includes, in the form in which it is sold, a sterilizing or disinfecting solution, and which can be used one time for sterilizing contact lenses, and then discarded.

It is a further object of the present invention to provide such a contact lens disinfecting container structure which is simple to use, and inexpensive to produce, yet which carries out the disinfecting or sterilizing to the desired degree.

It is a still further object of the present invention to provide such a lens disinfecting container structure which has a plurality of lens disinfecting containers separably attached to each other, so that they can be removed one at a time and used and then discarded.

These objects are achieved by a contact lens disinfecting container which has an open topped lens container, a piercer means mounted in the lens container and having piercing portions thereon projecting to the vicinity of the open top of the lens container, an open topped solution container attached to the lens container for being foldable over against the lens container with the open top thereof facing the open top of the lens container, a sterilizing or disinfecting solution in the solution container, a pierceable cover sealed to the edge of the solution container around the open top thereof and a catalyst in the lens container for decomposing the sterilizing agent in the solution. The piercer projects sufficiently toward the lens container when the solution container is folded over against the lens container to pierce the pierceable cover. The lens disinfecting containers can be separably joined to each other along the sides thereof and separated one at a time for use.

BRIEF DESCRIPTION OF THE DRAWINGS

Other and further objects of the invention will become apparent from the following specification, taken together with the accompanying drawings, in which:

FIG. 1 is a side elevation view, partly in section, of a contact lens disinfecting container structure according to the present invention;

FIG. 2 is a top plan view of the container structure of FIG. 1, with the covers for the respective containers removed;

DETAILED DESCRIPTION OF THE INVENTION

Figure 3:
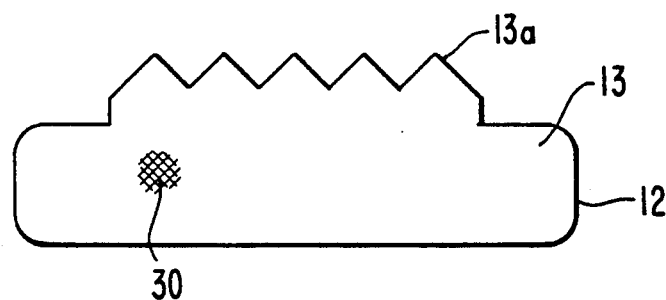
FIG. 3 is a side elevation view of piercer which forms part of the container structure according to the present invention.

The contact lens disinfecting container structure of the present invention comprises, as shown in FIGS. 1 and 2, an open topped lens container 10, here shown to be generally rectangular in shape, and having a flange 11 around the edge of the open top thereof. The lens container has a piercer means therein, which is in the form of a piercer 12 having a flat plate shape, and having a body portion 13 and upwardly projecting piercing projections 14. The piercer 12 is removably mounted in the lens container 10 in piercer retainers 14 on opposite walls of the lens container 10, each of which has a slot 15 therein into which the pierce body portion 13 can be inserted to hold the piercer 12 upright in the lens container 10 with the piercing projections 14 in the vicinity of the open top of the lens container 10.

An open topped solution container 16 is provided which has an outwardly and downwardly projecting lip 17 around the periphery thereof and an outwardly projecting flange 18 on the bottom edge of the projecting lip 17. The projecting lip has a sealing surface 17a thereon which is adapted to have a solution container cover 23 removably sealed thereto for sealing a sterilizing or disinfecting solution 19 in the solution container. The solution container cover 23 is made of a pierceable material capable of being pierced by the piercing projections 14 on the piercer 12.

The flange 11 is joined to the flange 18 by a hinge 19 around which the solution container 16 can be folded so that the open top thereof is facing the open top of the lens container 10.

Preferably the piercer 12 divides the interior of the lens container into two separate contact lens receiving parts 10a and 10b, each of which is large enough to receive a contact lens L, shown in phantom lines in FIG. 2. Further, it is preferable that the lens container 10 have a lens cover 20 sealingly detachably connected to the flange 11.

Figure 5:
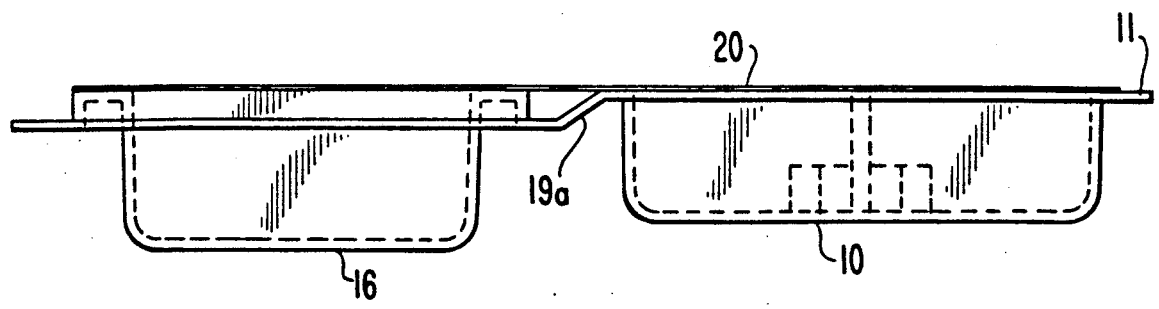
FIG. 5 is a side elevation view of a modified form of the container structure of FIG. 1.
Figure 6:
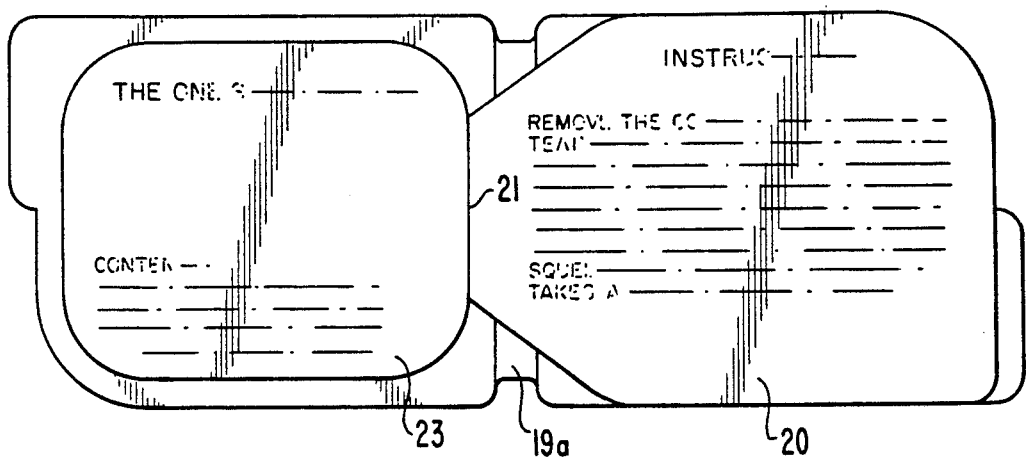
FIG. 6 is a plan view of the container structure of FIG. 5.

In a further preferred embodiment, as shown in FIG. 5, the hinge portion, here shown as 19a between the lens container 10 and the solution container 16 is angled downwardly and lowers the top surface 17a of the lip 17 to the level of the flange 11 around the periphery of the open top of the lens container 10. The lens container cover 20 in this embodiment is detachably joined to the solution container cover 18 along a junction line 21 for reasons which will be described hereinafter.

The lens container 10, hinge 19 and solution container 16 are preferably molded from a flexible plastic material which is impervious to the sterilizing or disinfecting solution which is to be contained in the solution container 16, such as, for example, polypropylene. The piercer 12 and the retainers 14 can be similarly of molded plastic material such as polypropylene. The solution container cover 18 is preferably a metal foil which can be easily peeled from the surface 17a of the lip 17, and has a plastic coating on the under surface thereof to protect it from the solution 19. The lens container cover 20 can be a plastic backed paper or the like which is easily peeled from the flange 11. These covers are preferably removably adhered to the flanges by an appropriate adhesive material which permits the covers to be peeled back from the tops of the containers.

The solution to be provided in the solution container 16 can be an opthalmic solution containing hydrogen peroxide, sodium chloride, and stabilizing components such as sodium stannate, sodium nitrate, and can be buffered with phosphates.

In use, the container structure is provided with the piercer 12 lying in the bottom of the lens container 10, and the first step is to peel the lens container cover 20 from the lens container 10, and then insert the edges of the piercer 12 into the slots 15 in the retainers 14 with the piercing projections 13a pointing upwardly. The contact lenses of a pair of contact lenses are then placed in the respective lens receiving parts 10a and 10b, and the solution container 16 is folded over to the position of FIG. 4, in which position the piercing projections 13a pierce the solution container cover 23 to allow the solution 19 to drain from the now inverted solution container 16 into the lens container and to cover the lenses L therein. The structure is left in this condition until the lenses are sterilized.

Figure 4:
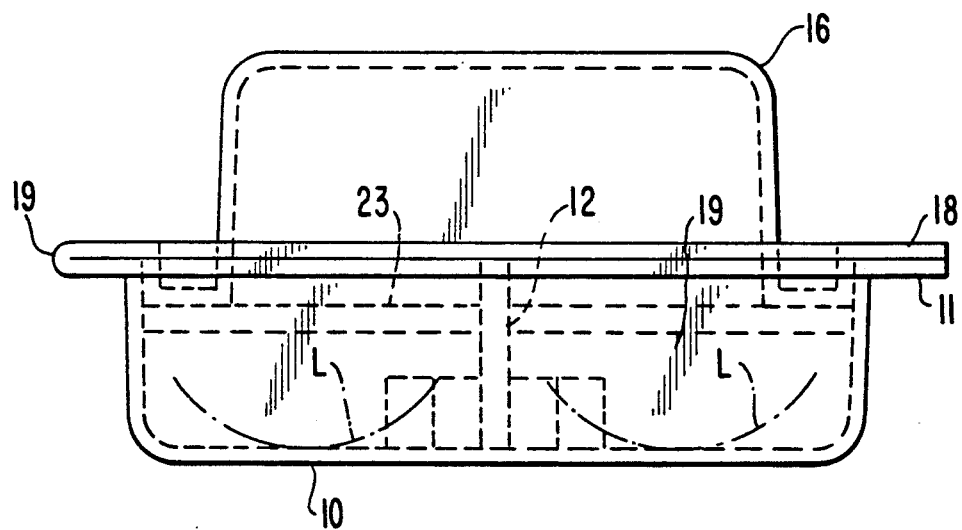
FIG. 4 is a side elevation view of the container structure of FIGS. 1 and 2 with the solution container folded over against the lens container in the operating position of the container structure.

A catalyst means is provided in the lens container 10 for decomposing the sterilizing agent in the solution, so that the solution is neutralized, as the solution 19 stands in the lens container 10 as shown in FIG. 4, the solution is gradually neutralized, until it is completely neutral.

At this point, the solution container 16 can be turned back, and the lenses L removed from the lens container 10, and the container structure can then be discarded.

The preferred arrangement is to have the catalyst as a coating of platinum, shown schematically at 30 on the piercer 12 in FIG. 3. Since the solution container 16 is designed to hold only about 10 milliliters of solution, the platinum coating can be of a micron thickness in an amount sufficient just to neutralize this small amount of solution.

Obviously, the catalyst could also be provided in other positions within the container 10, such as along one wall, or on the bottom thereof.

The embodiment of FIG. 5 differs from that of FIGS. 1-4 in that the lens cover 20 when it has been peeled from the flange 11 must then be separated from the solution container flange 18 by detaching it along the separation line 21. In this arrangement, it is obviously preferable to have the lens container cover 20 made from the same type of metal foil as the solution container flange 18. It will be seen that this arrangement is possible because the lens container cover 20 and the solution container flange 18 lie in the same plane along the top of the structure, the flange 18 being positioned below the level of the covers.

It will be further observed that the top of the solution container 16 has a size and shape such that it fits down into the open top of the lens container 10. The flange 18 thus engages the flange 11 of the lens container 10 and acts as a stop for stopping the descent of the solution container 16 into the lens container 10.

Figure 7:
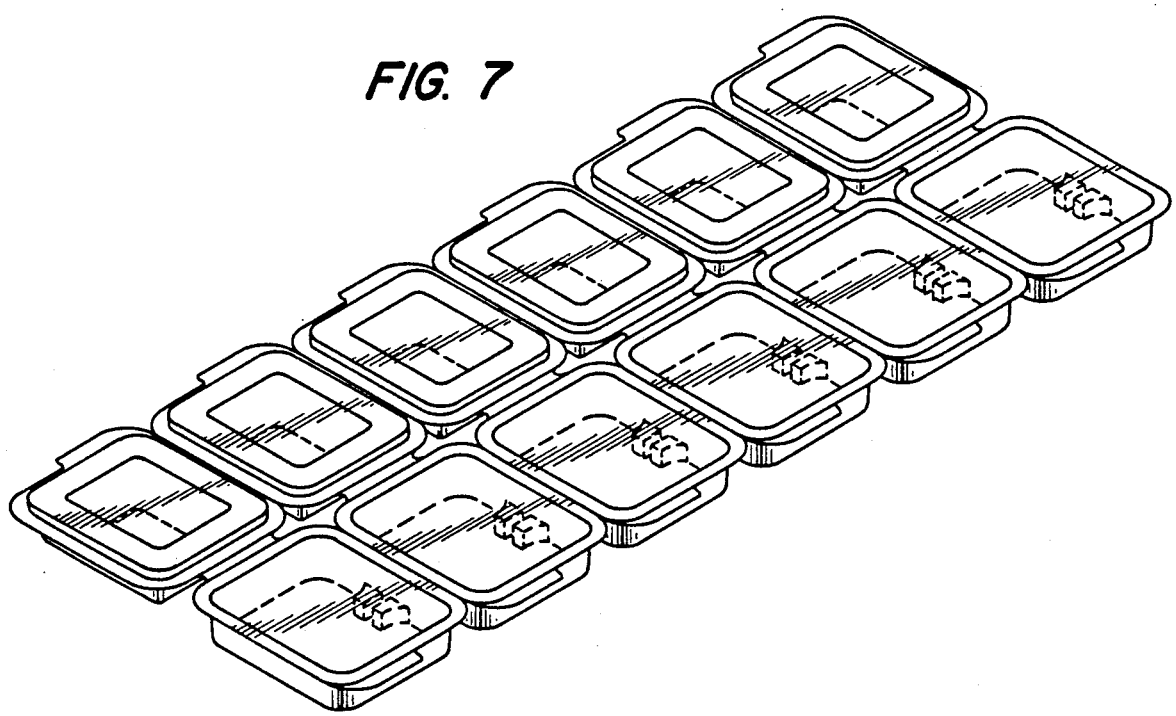
FIG. 7 is a perspective view of a plurality of lens disinfecting containers detachably connected side by side in a package.

The container structures of FIGS. 1-4 and FIGS. 5 and 6 can be detachably joined side by side into a package of a plurality of lens disinfecting containers as shown in FIG. 7. Thus, the user can detach a single lens disinfecting container for use, leaving the remainder attached for storage until it is desired to use another one.

It will thus be seen that there has been provided a one-time-use lens disinfecting container which can quickly and easily sterilize a pair of contact lenses, and can then be discarded. The device is compact and easy to use, and can be made inexpensively so that it can be sold at a reasonable price and discarded after a single use. Moreover, since the container is a one use type device, there is no problem of the growth of bacteria, which problem occurs with reusable devices for sterilizing lenses.

We claim:
1. A contact lens disinfecting kit comprising:
an open topped lens container;
an elongated piercer mounted in said lens container in an upright position and having piercing portions thereon projecting to the vicinity of the open top of said lens container, said piercer dividing the interior of said lens container into two separate contact lens receiving parts;
an open topped solution container attached to said lens container for being foldable over against said lens container with the open top thereof facing the open top of the lens container and having a shape with a peripheral edge around the open top thereof which fits snugly into the open top of said lens container;
a sterilizing or disinfecting solution in said solution container;
a pierceable cover sealed to the edge of said solution container around the open top thereof;
said piercer means projecting sufficiently toward said solution container when said solution container is folded over against said lens container to pierce said pierceable cover; and catalyst means in said lens container for decomposing the sterilizing agent in said solution.

2. A contact lens disinfecting kit as claimed in claim 1 in which said piercer is a plate shaped member, and said lens container has slotted retainers therein in which said piercer is removably positioned.

3. A contact lens disinfecting kit as claimed in any one of claims 1 and 2 in which said catalyst means is a coating of catalyst material on said piercer means.

4. A contact lens disinfecting kit as claimed in claim 1 in which said piercer extends only to the top of said lens container.

5. A contact lens disinfecting kit as claimed in claim 1 in which said solution container has a laterally outwardly projecting flange around the outside thereof below the open top thereof for engaging an upper edge of said lens container when said solution container is folded over against said lens container, whereby said flange acts as a stop for limiting the movement of said solution container into said lens container.

6. A contact lens disinfecting kit as claimed in claim 4 or 5 in which said piercer is a plate shaped member, and said lens container has slotted retainers therein in which said piercer is removably positioned.

7. A contact lens disinfecting kit as claimed in claim 4 or 5 in which said catalyst means is a coating of catalyst material on said piercer.

8. A contact lens disinfecting kit as claimed in claim 4 or 5 further comprising a hinge means between said lens container and said solution container and extending from the edge of the open top of said lens container to said solution container at a level below the top of said solution container, and a lens container cover removably attached to said lens container and being separably joined to said piercable cover.

9. A contact lens disinfecting kit as claimed in claim 6 further comprising a hinge means between said lens container and said solution container and extending from the edge of the open top of said lens container to said flange on said solution container at a level below the top of said solution container, and a lens container cover removably attached to said lens container and being separably joined to said piercable cover.

10. A contact lens disinfecting structure comprising:

an open topped lens container;

an elongated piercer mounted in said lens container in an upright position and having piercing portions thereon projecting to the vicinity of the open top of said lens container, said piercer dividing the interior of said lens container into two separate contact lens receiving parts;

an open topped solution container attached to said lens container for being foldable over against said lens container with the open top thereof facing the open top of the lens container and having a shape with a peripheral edge around the open top thereof which fits snugly into the open top of said lens container;

a sterilizing or disinfecting solution in said solution container;

a pierceable cover sealed to the edge of said solution container around the open top thereof;

said piercer means projecting sufficiently toward said solution container when said solution container is folded over against said lens container to pierce said pierceable cover; and catalyst means in said lens container for decomposing the sterilizing agent in said solution;

said plurality of lens disinfecting kits being separably joined to each other along the sides of said lens containers and said solution containers other than the edges along which they are foldably attached.

* * * * *